United States Patent [19]
Goulding et al.

[11] Patent Number: 5,892,808
[45] Date of Patent: Apr. 6, 1999

[54] METHOD AND APPARATUS FOR FEATURE DETECTION IN A WORKPIECE

[75] Inventors: John R. Goulding; Cary S. Kiest, both of Albany; Joseph G. LaChapelle, Philomath, all of Oreg.

[73] Assignee: Techne Systems, Inc., Albany, Oreg.

Related U.S. Application Data

[60] Provisional application No. 60/022,019, Jun. 28, 1996.

[21] Appl. No.: 789,955

[22] Filed: Jan. 30, 1997

[51] Int. Cl.$^6$ .................................................. G01N 23/04
[52] U.S. Cl. ................................ 378/63; 378/58; 382/152
[58] Field of Search ........................ 378/58, 63; 364/507; 382/152

[56] References Cited

U.S. PATENT DOCUMENTS

| | | | |
|---|---|---|---|
| 3,120,861 | 2/1964 | Finlay et al. | |
| 3,471,702 | 10/1969 | VanVeld | 250/219 |
| 3,574,470 | 4/1971 | Paine | 356/209 |
| 3,591,291 | 7/1971 | Grear-Ypsilanti | 356/120 |
| 3,694,658 | 9/1972 | Watson et al. | 250/219 DF |
| 3,849,793 | 11/1974 | Ablett | 358/81 |
| 3,890,509 | 6/1975 | Maxey. | |
| 3,970,128 | 7/1976 | Kohlberg | 144/245 A |
| 3,983,403 | 9/1976 | Dahlström et al. | 250/560 |
| 4,086,496 | 4/1978 | Berry | 250/561 |
| 4,092,068 | 5/1978 | Lucas et al. | 356/73 |
| 4,097,159 | 6/1978 | Strandberg | 356/167 |
| 4,097,160 | 6/1978 | Yataki et al. | 356/237 |
| 4,149,089 | 4/1979 | Idelsohn et al. | 250/563 |
| 4,184,175 | 1/1980 | Mullane, Jr. | 358/93 |
| 4,196,648 | 4/1980 | Jones et al. | 83/365 |

(List continued on next page.)

OTHER PUBLICATIONS acumen Incorporated; *900 Series Programmer's Guide* (1991).

Durand–Raute; *Durand–Raute Product Bulletin; The Microvision SO–2000 Takes the Guesswork out of Grading* no date.

Innovative Vision AB; Brochure; *Woodeye; An Automatic Inspection System for Improved Quality and Greater Profits in the Timber Industry* no date.

*Primary Examiner*—David P. Porta
*Assistant Examiner*—David Vernon Bruce
*Attorney, Agent, or Firm*—Klarquist Sparkman Campbell Leigh & Whinston LLC

[57] ABSTRACT

A feature detection apparatus includes a reflective imaging system, a transmissive imaging system, and memory for generating an image of a workpiece. The reflective imaging system generates a first bit image of a surface of the workpiece. The transmissive imaging system generates a second, different bit image of the density of the workpiece. The two images are then combined in memory into a more complete image that contains data describing the surface and interior of the workpiece. The apparatus also includes a filter for enhancing the combined bit image so that physical features of the workpiece are accurately detected. The filter is constructed to perform the following steps. For detecting a feature of interest, the filter determines a mean, standard deviation, and normal distribution of the image's pixel intensities. The filter then uses the normal distribution to map the pixel intensities above the mean to one set of enhanced pixel intensities and to map pixel intensities below the mean to another set of enhanced pixel intensities. Pixels of the enhanced image are sampled to determine if a pixel meets a threshold intensity for the feature being sought. For a pixel that meets the threshold intensity, a feature detection operation is applied to the pixel and its neighboring pixels to determine if the feature is present in the image. If so, the full extent of the detected feature is then determined.

19 Claims, 13 Drawing Sheets

5,892,808
Page 2

U.S. PATENT DOCUMENTS

| | | | |
|---|---|---|---|
| 4,199,261 | 4/1980 | Tidd et al. | 356/448 |
| 4,274,288 | 6/1981 | Tittmann et al. | 73/602 |
| 4,286,880 | 9/1981 | Young | 356/431 |
| 4,294,149 | 10/1981 | Olsson | 83/435.1 |
| 4,300,836 | 11/1981 | Holmes et al. | 356/376 |
| 4,403,294 | 9/1983 | Hamada et al. | 364/507 |
| 4,412,746 | 11/1983 | Yokouchi | 356/446 |
| 4,424,530 | 1/1984 | Taylor | 358/96 |
| 4,498,778 | 2/1985 | White | 356/376 |
| 4,518,259 | 5/1985 | Ward | 356/446 |
| 4,606,645 | 8/1986 | Matthews et al. | 356/446 |
| 4,800,287 | 1/1989 | Green, Sr. et al. | 250/560 |
| 4,801,207 | 1/1989 | Williams | 356/376 |
| 4,803,371 | 2/1989 | Durland | 250/566 |
| 4,827,142 | 5/1989 | Hatje | 250/563 |
| 4,858,156 | 8/1989 | Martin | 364/560 |
| 4,879,752 | 11/1989 | Aune et al. | 382/1 |
| 4,899,356 | 2/1990 | Berry et al. | 378/58 |
| 4,916,629 | 4/1990 | Bogue et al. | 364/507 |
| 4,926,350 | 5/1990 | Bechtel et al. | 364/550 |
| 4,940,850 | 7/1990 | Satake | 209/580 |
| 4,984,172 | 1/1991 | Laminari | 364/478 |
| 4,992,949 | 2/1991 | Arden | 364/478 |
| 5,023,805 | 6/1991 | Aune et al. | 364/507 |
| 5,078,496 | 1/1992 | Parker et al. | 356/371 |
| 5,412,220 | 5/1995 | Moore | 250/563 |
| 5,703,960 | 12/1997 | Soest | 382/141 |

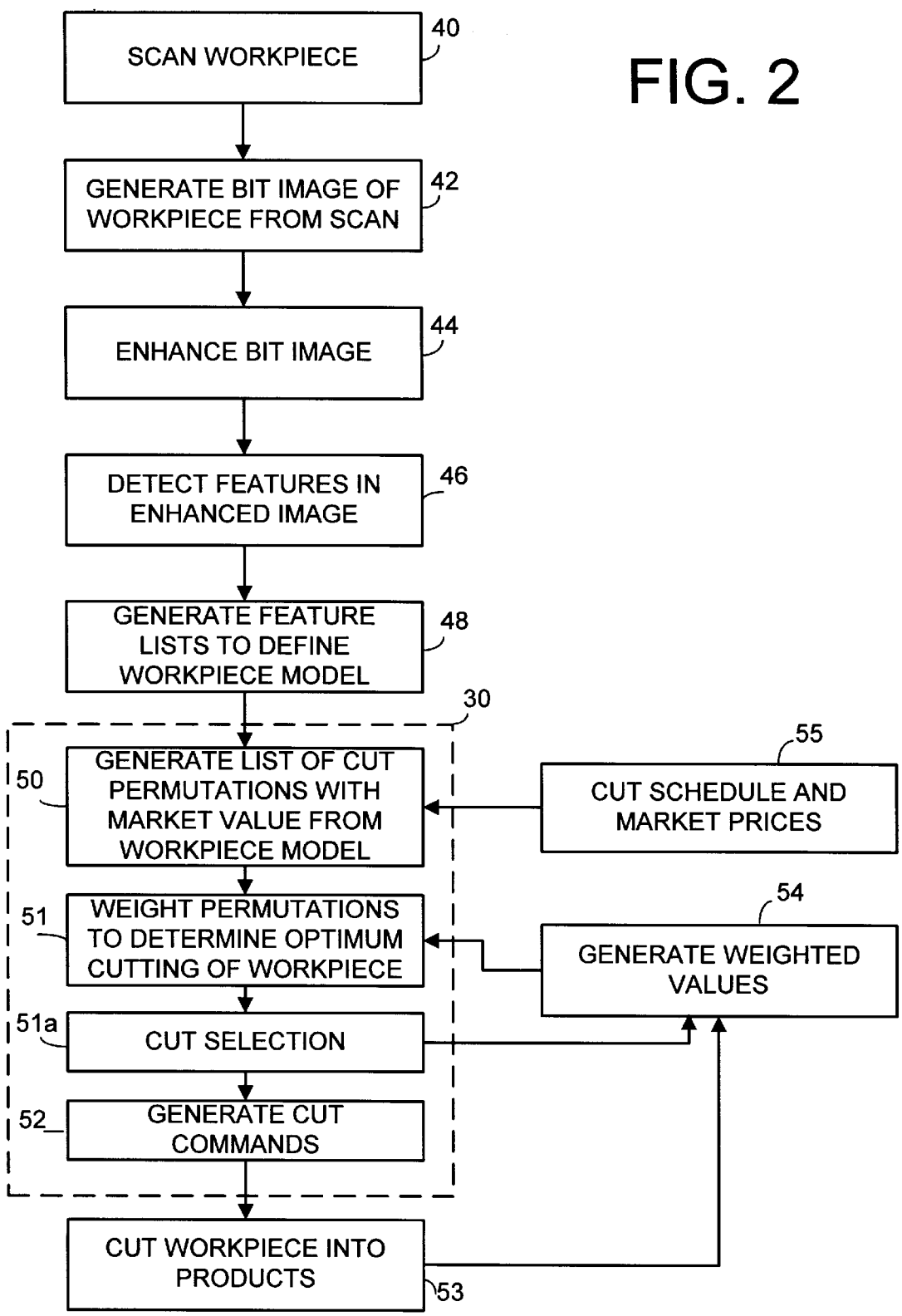

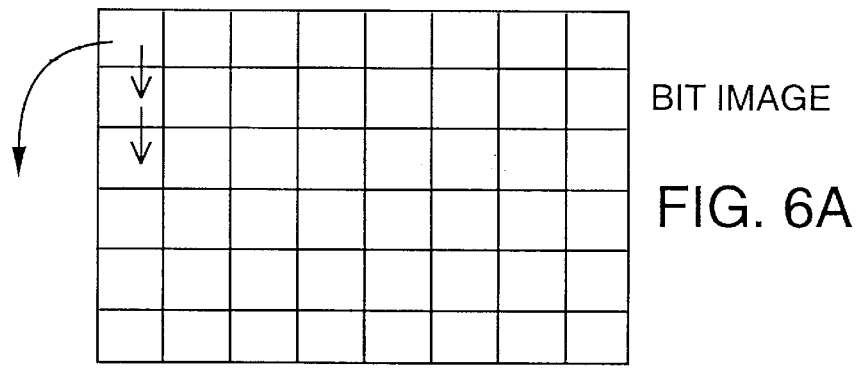
BIT IMAGE
FIG. 6A
FIG. 6B
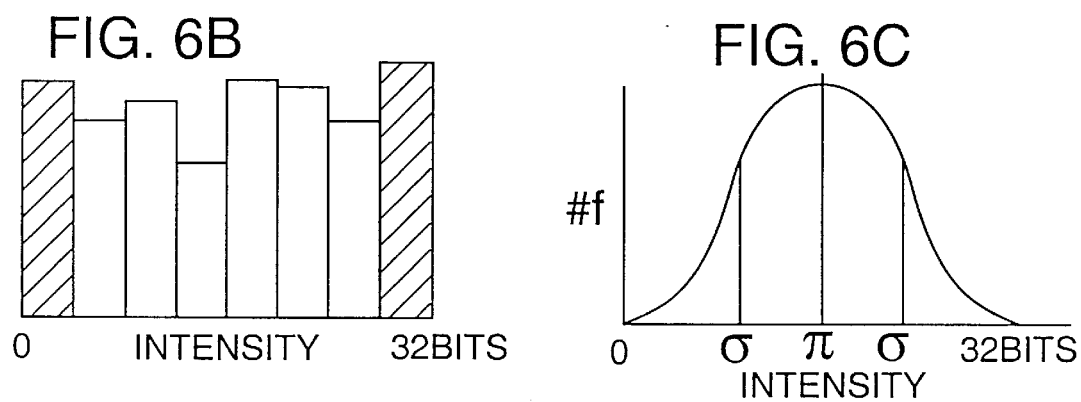
FIG. 6C
FIG. 6D
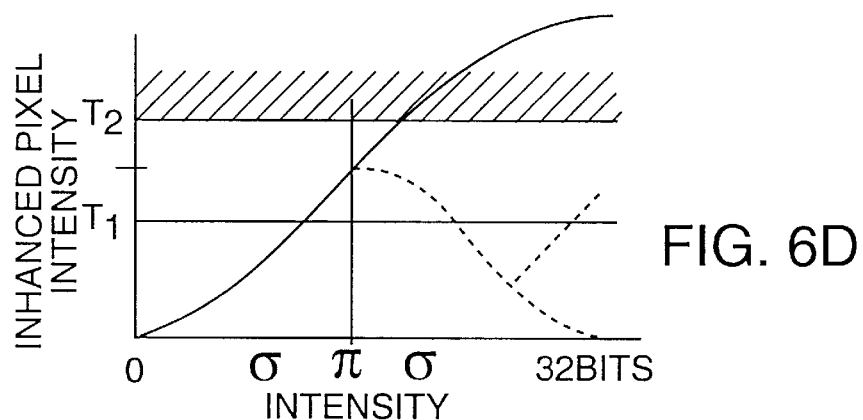
ENHANCED IMAGE
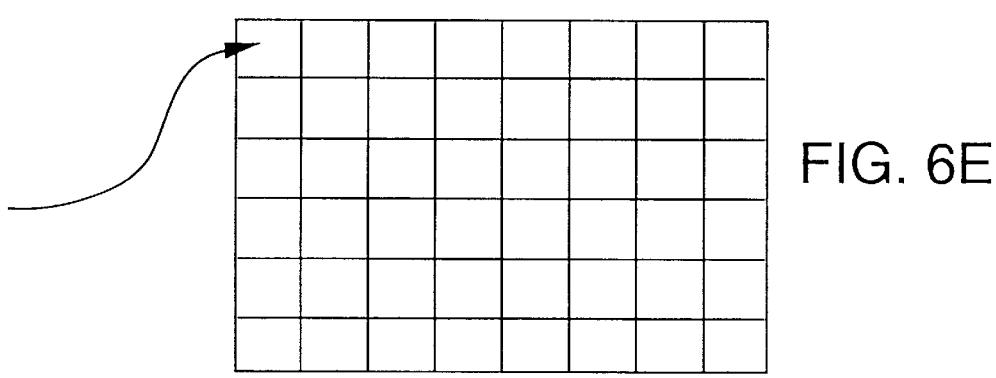
FIG. 6E

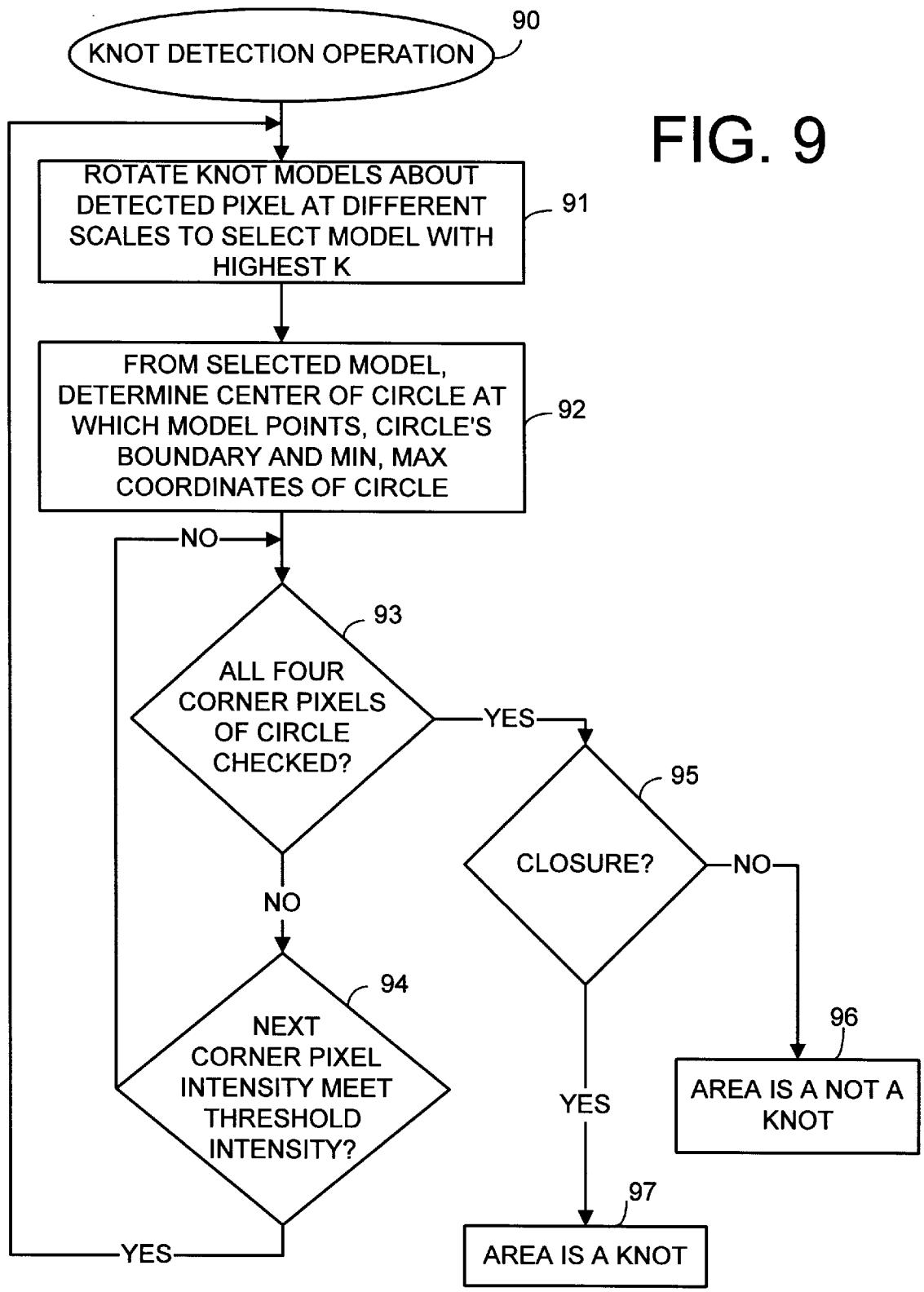

METHOD AND APPARATUS FOR FEATURE DETECTION IN A WORKPIECE

TECHNICAL FIELD

This application is based on U.S. Provisional Patent application Ser. No. 60/022,019, filed Jun. 28, 1996.

This invention relates generally to detecting features such as defects in a workpiece that is to be cut into constituent products. More particularly, this invention relates to detecting defects in a workpiece such as wood and with that information cutting the workpiece into an optimum mix of products such as boards of various widths, lengths and grades.

BACKGROUND OF THE INVENTION

Traditionally, defects in a workpiece such as wood were found by manually inspecting the workpiece. Based on that inspection and a knowledge of the type of products desired, cuts were made to the workpiece to produce products. For example, in the case of wood products, a person would inspect a piece of wood for knots and based on that inspection and a knowledge of the type of boards desired, make certain cuts to the wood.

To improve the speed and accuracy of defect detection, various machines have been developed that use cameras and computers to automatically find defects in the workpiece. The most effective of these systems create a gray scale bit mapped image of the workpiece and then test the pixels of the image against a threshold pixel intensity. Pixels that meet the threshold intensity are considered defects. These systems, however, have proven to lack consistency and accuracy when presented with the wide variations in workpiece color. For example, these systems cannot accurately distinguish heavy grain in wood from a knot. While both are darker than clear wood, only the knot is considered a defect.

Deciding what cuts to make to a workpiece has also been automated to some degree. Machines now keep track of the products cut and the production goal. This information is provided to the cutter (human or machine) to influence the cuts made to the next workpiece. For example, the production goal might be certain numbers of wood pieces of certain sizes and grades. As wood is cut into products, the numbers of wood pieces cut of each size are updated and compared to the production goal. Cuts are then made to move toward the production goal as rapidly as possible without exceeding it.

The drawback of present approaches to optimizing workpiece cutting is the time required for determining the optimum cuts. A workpiece such as wood may be cut into any number of different-sized products of different grades. A decision still must be made as to what specific cuts to make to the workpiece to provide the desired products. If the decision is by a human operator, then production is delayed. If the decision is by a human operator or a machine based solely on the information noted above, then the decision does not take into account the value of products cut from each individual workpiece.

An objective of the invention, therefore, is to improve the detection of features such as defects in a workpiece. Another objective of the invention is to optimize the cutting of a workpiece into products that provide the greatest value at the time the workpiece is cut.

SUMMARY OF THE INVENTION

An apparatus and method for generating an image of a workpiece in accordance with the invention includes a reflective imaging system, a transmissive imaging system, and memory. The reflective imaging system generates a first bit image of a surface of the workpiece.

The pixels of the first bit image are represented by a number of bits. The transmissive imaging system generates a second, different bit image of the density of the workpiece, with the pixels of this image also represented by a number of bits. The two images are then combined in memory into a combined, more complete image that contains data describing the surface and interior of the workpiece. With that information, the workpiece can be cut to optimum-sized lengths and widths.

Apparatus in accordance with the invention may also include a filter for enhancing the combined bit image so that physical features of the workpiece are accurately detected. The filter is constructed to perform the following steps. For a feature of interest, the filter determines a mean, standard deviation, and normal distribution of the image's pixel intensities. The filter then uses the normal distribution to map the pixel intensities above the mean to one set of enhanced pixel intensities and to map pixel intensities below the mean to another set of enhanced pixel intensities. The enhanced image that results is stored in memory for use in feature detection.

A feature detection method in accordance with the invention samples pixels of the complete image (preferably but not necessarily enhanced) to determine if a pixel meets a threshold intensity for the feature being sought. For a pixel that meets the threshold intensity, a feature detection operation is applied to the pixel and its neighboring pixels to determine if the feature is present in the image. If so, the full extent of the detected feature is then determined.

The foregoing and other objects, features, and advantages of the invention will become more apparent from the following detailed description of a preferred embodiment which proceeds with reference to the accompanying drawings.

BRIEF DESCRIPTION OF THE DRAWINGS

FIG. 2 is a flowchart of a method of cutting workpieces according to the invention.

FIGS. 6A–E illustrate the method of FIG. 5 for enhancing an image for one type of feature such as internal defects in wood.

FIG. 9 is a flowchart for applying a knot detection operation to an image of a piece of wood.

DETAILED DESCRIPTION OF PREFERRED EMBODIMENTS

Figure 1:
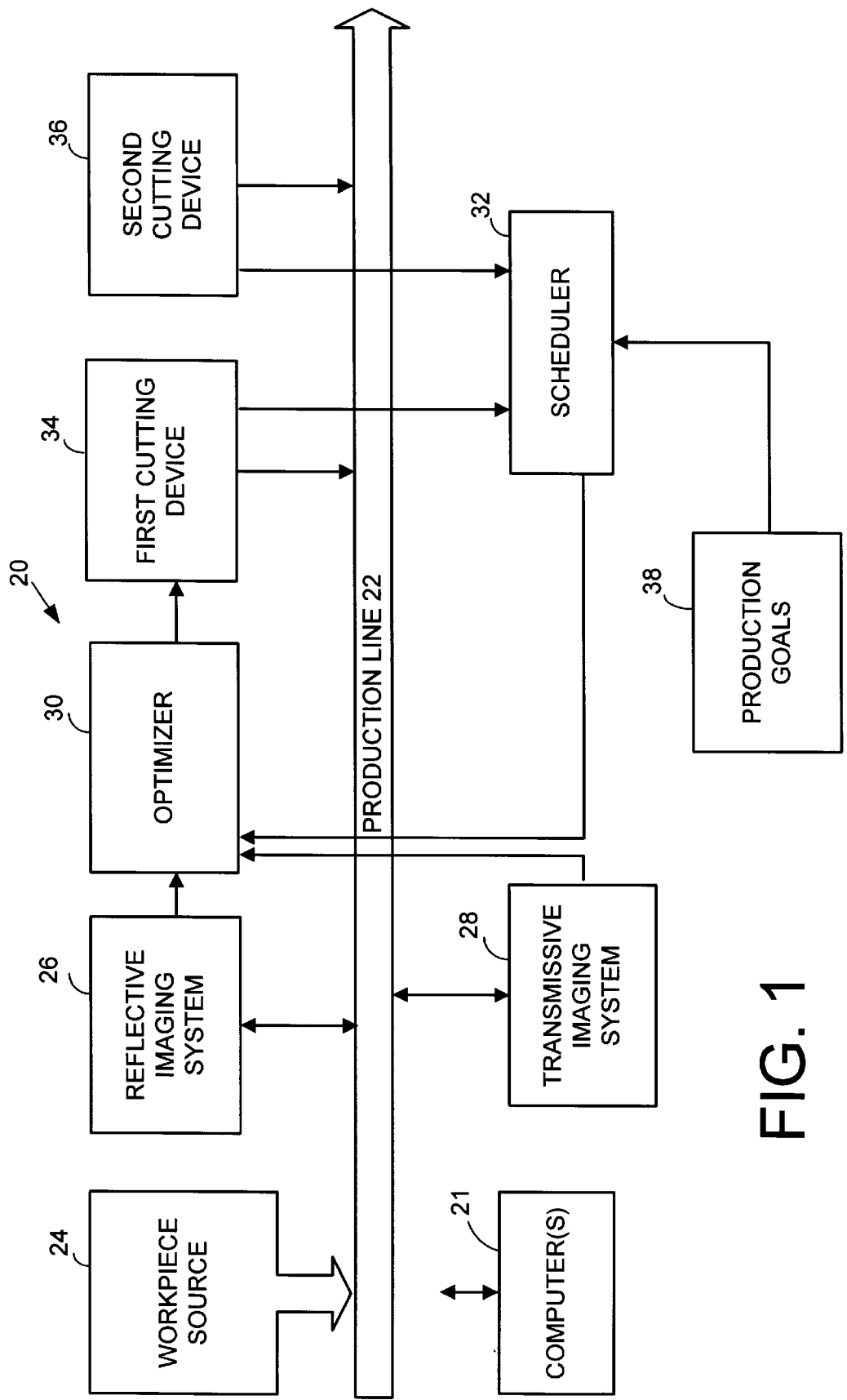
FIG. 1 is a block diagram of a workpiece cutting system for cutting workpieces according to the invention.

FIG. 1 is a block diagram of a workpiece cutting system 20 for cutting workpieces according to the invention. The system 20 may be configured for cutting different types of workpieces, with the illustrated embodiment designed for cutting pieces such as wooden boards into lumber of various widths, lengths and grades. Included within the cutting system 20 is a block 21 labeled computer(s), which represents the one or more computers that may be utilized throughout the system, depending upon the system implementation preferred by one of skill in the art. For example, each of the system's elements to be described may itself be computerized or the elements may be linked to one or more computers instead.

Also within the system 20 is a production line 22 on which workpieces are loaded from a source 24 such as a stack of boards. From the load point each workpiece is transported past scanners such as a reflective imaging system 26 and a transmissive imaging system 28 that scan the workpiece for features of interest.

The reflective imaging system 26 in the preferred embodiment comprises a number of cameras or equivalent devices for capturing a black-and-white or color image of the workpiece from light that is reflected by the workpiece surfaces. Equivalent reflective imaging systems that rely on a reflected signal include sonic systems or systems that use non-visible portions of the electromagnetic spectrum that reflect from a workpiece surface. For boards, the reflective imaging system captures features such as board dimensions, wane, surface stain, knots, splits, etc. as parts of the image.

The transmissive imaging system 28 comprises an X-ray, microwave or equivalent devices that create an internal image of the workpiece. Equivalent devices include ultrasound, nuclear magnetic resonance (NMR), or computed tomography (CT) devices. For boards, the transmissive imaging system captures features such as internal knots, pitch pockets, air pockets, and abnormal density regions within the board as parts of the image. In the present embodiment, the surface and interior images are first and second bit images. The surface image has a given number of bits per color per pixel such as eight red, eight blue and eight green, and the interior image has a number of bits per pixel such as eight indicating the density of the workpiece. Other number of bits can, of course, be used. These images are combined and stored as a combined, more complete bit image of the workpiece in computer memory.

The image of the workpiece is provided to an optimizer 30 that determines which cuts to make to the workpiece to provide products of the present greatest value. In the context of cutting boards in system 20, these cuts are rip cuts for cutting the boards into specified widths. To make that determination, the optimizer relies on several sources of information including present market values for products, the types of products that can be made, production goals for the present run of workpieces, production to date, and production rate. Much of this information is provided to the optimizer by a scheduler 32 that generates input to the optimizer based on feedback from cutting devices 34 and 36 as to the number and types of cuts made and on material information 38. The scheduler's method of control uses the production rate, rate of consumption, and consumption goal as feedback to adjust the weights. Other information such as market prices is provided directly to the optimizer by the system manager. Based on this dynamic information, the optimizer generates cut commands for a first cutting device 34. A second cutting device 36 may also be responsive to cut commands depending upon the degree of automation of the system 20. In the present embodiment of system 20 for cutting boards, optimizer 30 generates rip commands for controlling a rip saw. The boards then move along production line 22 to cut tables where human operators use chop saws (second cutting devices 36) to cut the ripped boards to lengths predicted by the optimizer. However, it is possible to replace the human operators with a second cutting device directly responsive to the optimizer.

The optimizer 30 sends production information to the scheduler 32.

FIG. 2 is a flowchart showing in more detail how workpieces are cut according to the invention. As mentioned above with reference to FIG. 1, each workpiece is scanned (step 40) and a bit image is generated from the scan (step 42). Before the image is provided to the optimizer 30, however, it is enhanced and features of interest in the image are detected and listed in a workpiece model.

Figure 4:
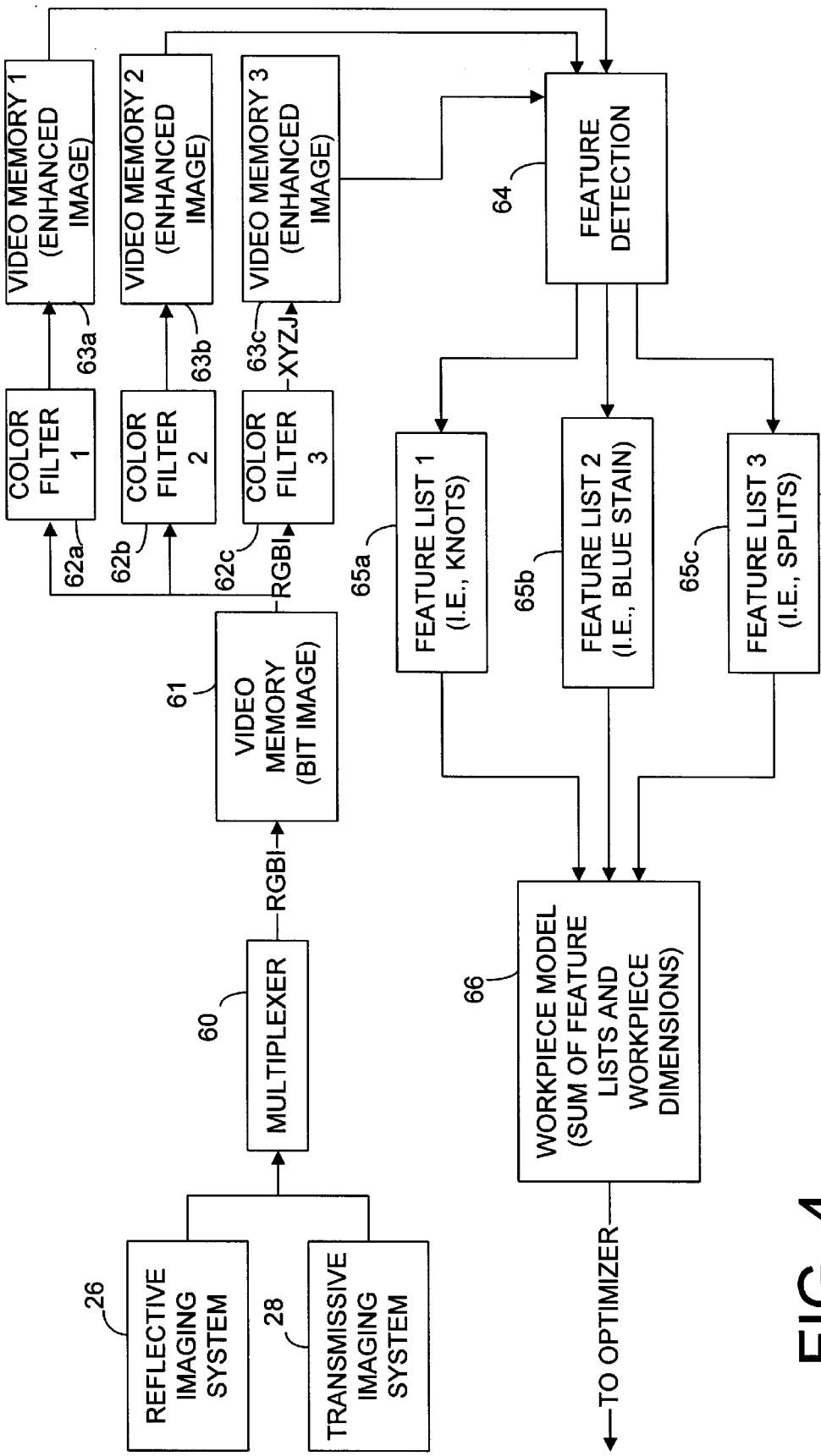
FIG. 4 is a block diagram of how a model of a workpiece is constructed from an initial image for use in cutting the workpiece.

FIGS. 4–7 illustrate the structure and method for enhancing the workpiece image. FIG. 4 is a block diagram of how a model of a workpiece is constructed from an initial image for use in cutting the workpiece. As part of the construction, an original bit image of the workpiece is enhanced. The scanned information from the reflective imaging system 26 and transmissive imaging system 28 is multiplexed via a multiplexer 60 and stored as a combined color bit image with red, green, blue and grey scale components (RGBI)in video memory 61. The stored image thus has a number of bits per pixel representing pixel intensity in color and grey scale.

Figure 5:
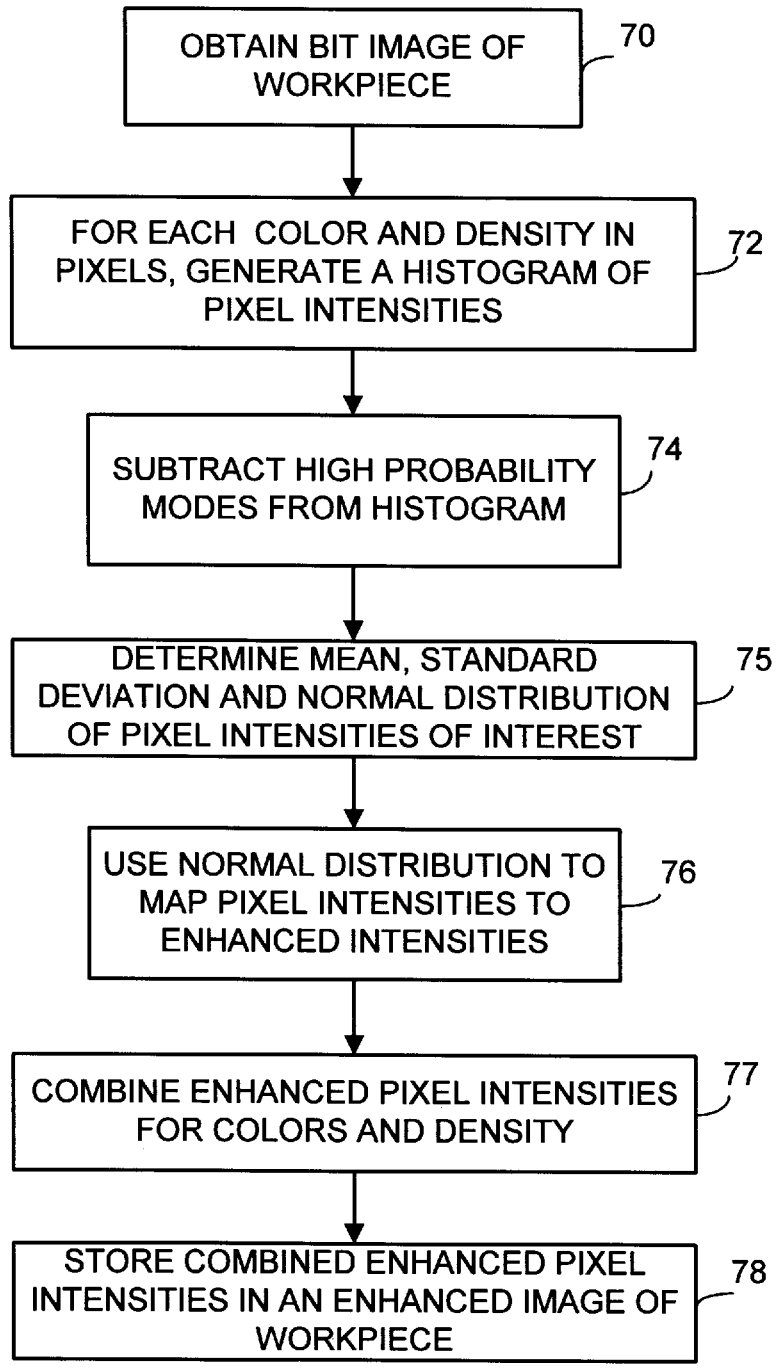
FIG. 5 is a flowchart of a method for enhancing a bit image of a workpiece for better feature detection.

A color filter 62a–c, which may be embodied in software, hardware, or a combination of both, enhances the image in the memory 61 in the manner shown in the flowchart of FIG. 5 and the graphs of FIGS. 6 and 7. The bit image is obtained from memory section by section (step 70) (FIG. 6A). A histogram of pixel intensities is then generated for each color and density in a pixel (step 72)(FIG. 6B). That is, in the present embodiment four histograms are generated, one for each of the three sets of color bits and for the set of density bits. The lower modes, or modes, have values corresponding to 0, 1, etc. and the higher modes have values corresponding to 29, 30, and 31 (if five bits per color) or 253, 254, 255 (if eight bits per color). The histogram illustrates the features of the image as measured by pixel intensity. For an image of a board surface, the histogram shows knots (lower intensities), grain (middle intensities), and clear (higher intensities). The blue histogram also contains "blue stain" as a set contained in grain and clear; hence, blue stain is found by finding grain and clear. The goal of the enhancement is to make the desired feature stand out from the rest of the image by enhancing the feature's corresponding intensities.

Enhancement proceeds by subtracting the higher and lower pixel intensities from the histogram (step 74)(FIG. 6B). The mean, standard deviation and normal distribution of the pixel intensities of interest are then determined (step 75), which depends on the feature of interest. The term "normal distribution" as used here is intended to cover the actual normal distribution as well as substantially similar distributions. If the feature of interest is a knot (high density), then the pixel intensities of interest are the remaining modes of the histogram. The mean, standard deviation and standard distribution are then determined for these modes as shown in FIG. 6C. These parameters are then used to map the grayscale values (pixel intensities) in the image to different values (step 76)(FIG. 6D), by transforming the normal distribution into a sigmoidal function (i.e., reflecting the distribution curve in the y direction about the mean and normalizing (to saturation)). Pixel intensities above the mean are mapped to one set of enhanced pixel intensities such as intensities of a higher value, where the set is determined by the threshold values T1 and T2. Similarly, pixel intensities below the mean are mapped to another set of pixel intensities such as intensities of a lower value. Initial thresholds for feature detection are established at the enhanced pixel intensities that correspond to the standard deviation of the distribution.

The equation for the normal distribution is:

$$f(x) = \frac{1}{\sigma\sqrt{2\pi}} e^{-(X-\mu)/2\sigma^2}$$

The equation for the sigmoid transformation is:

$$f(x) = \frac{1}{1 + e^{-(x-\mu)/2\sigma^2}}$$

where $\mu$ is the mean, $\sigma$ is the standard deviation, and $\sigma^2$ is the variance. Both equations are multiplied by the "saturation" scale factor.

Figure 7A:
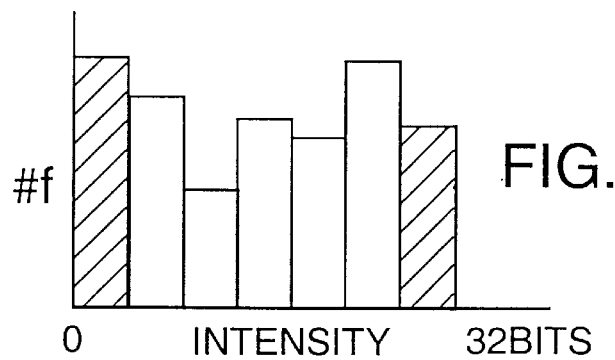
FIGS. 7A–E illustrate the method of FIG. 5 for enhancing an image for another type of feature such as surface knots in wood.
Figure 7B:
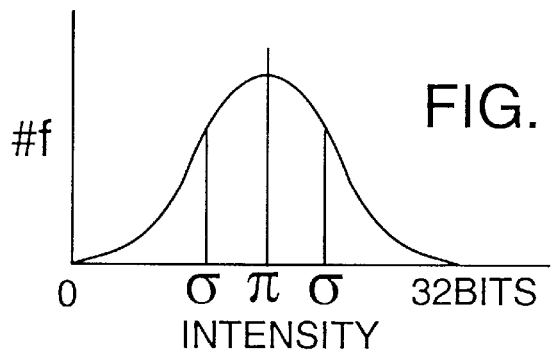
Figure 7C:
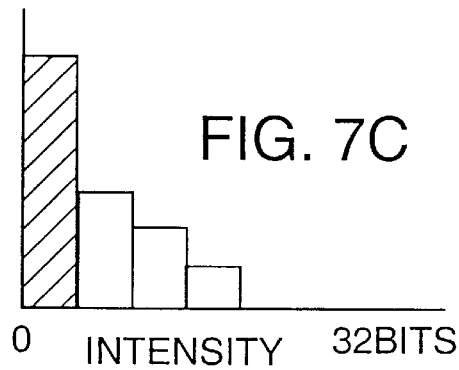
Figure 7D:
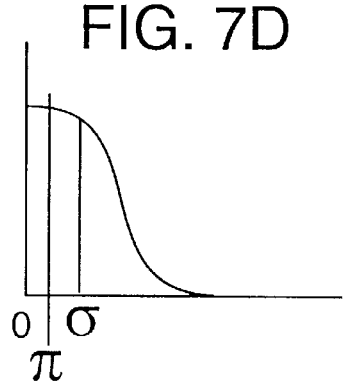
Figure 7E:
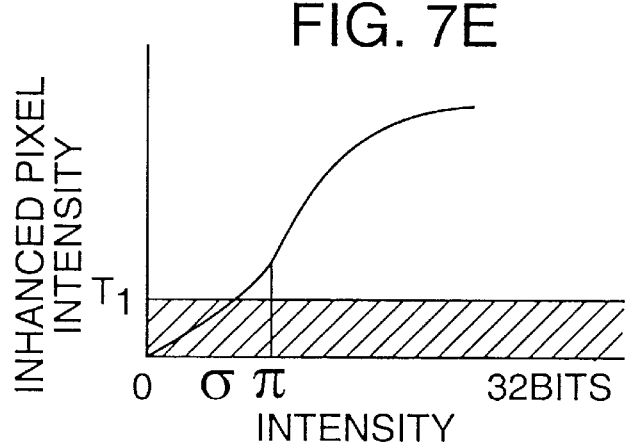

If the feature of interest is surface color, the normal distribution of interest is different. Referring to FIGS. 7A–E, once a normal distribution is obtained from the remaining modes of the histogram, the distribution is subtracted from the original histogram to obtain lower pixel intensities outside the normal distribution (FIG. 7C). The previously subtracted mode of lower pixel intensity is then added back to these lower pixel intensities (FIG. 7C). A mean, standard deviation and normal distribution of these lower pixel intensities are then determined (FIG. 7D). This distribution is then used to map the pixel intensities above the mean to higher pixel intensities and pixel intensities below the mean to lower pixel intensities.

The enhancement of pixel intensities is performed separately for the different colors and density and the results (enhanced intensities and thresholds) are combined to form a combined bit image (step 77). This enhanced image is then stored for feature detection (step 78), such as in video memory 63a–c (FIG. 4). For each feature of interest, an enhanced image is generated.

Figure 8:
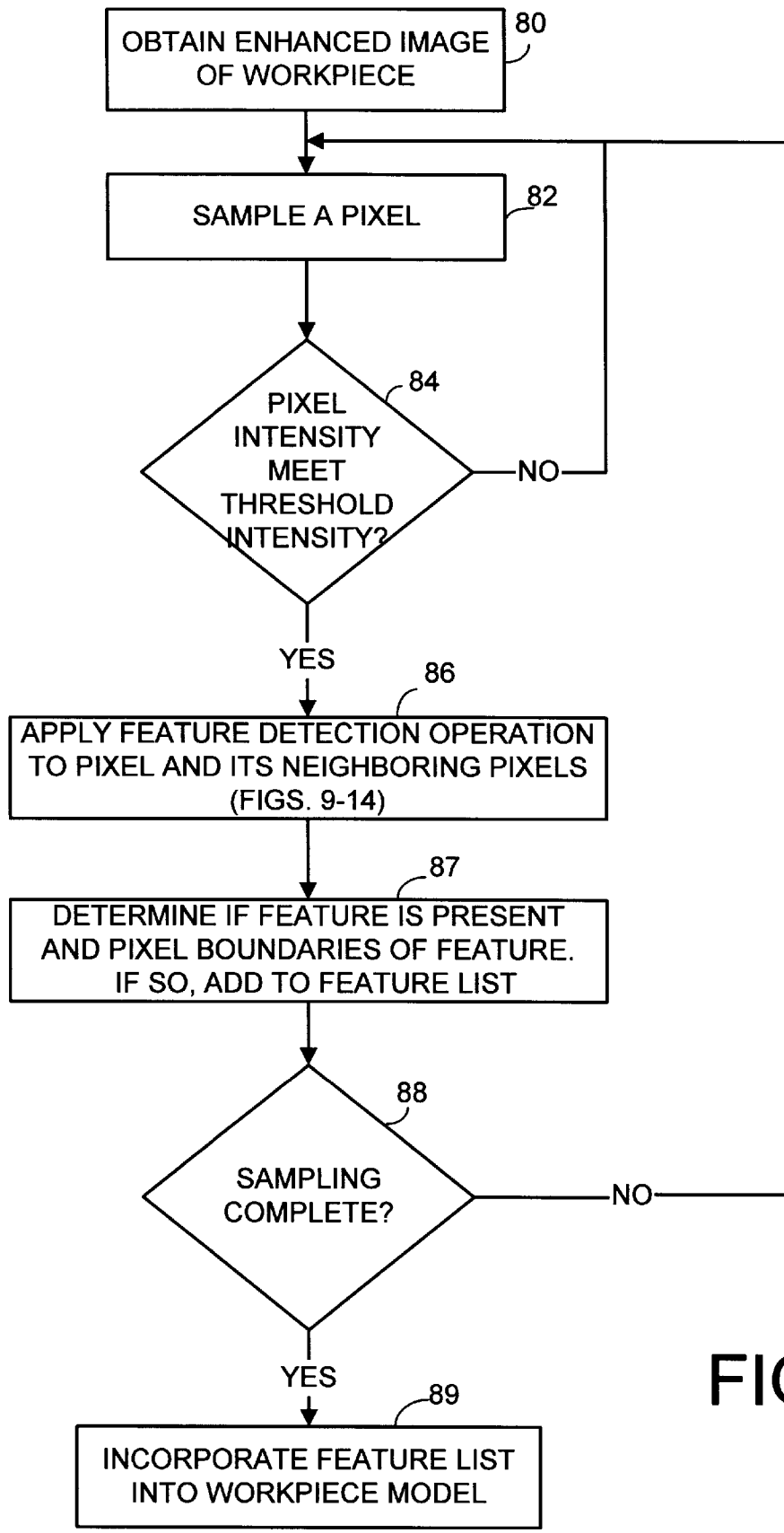
FIG. 8 is a flowchart of a method for detecting features in an image of a workpiece, including applying a feature detection operation to the image.

The enhanced image can now be examined to detect features of interest (steps 46, FIG. 2)(feature detection 64, FIG. 4). FIG. 8 illustrates the general process, with particular detection methods shown in FIGS. 9–14. The feature detection device, which may be implemented in software or hardware, obtains a copy of the enhanced image of the workpiece from video memory 63 (step 80). The enhanced image is them sampled according to a sampling scheme that depends upon the type of feature being sought, such as sampling every twelfth pixel in a raster scan vertically down the image (step 82). The pixel intensity of the sampled pixel is checked to see if it meets a threshold intensity that indicates the pixel may be part of a feature (step 84). If not, sampling continues through the image until such a pixel is found or the sampling is complete.

If the pixel intensity meets the threshold, the detection operation for the feature being sought is applied to the pixel and its neighboring pixels (step 86). There are a number of such operations that may be applied, depending upon the feature sought. Where the workpieces are boards, for example, there are different operations for detecting knots, blue stain, and splits.

From the operation it is determined if the feature is present and, if so, it is added to a feature list for the feature (step 87). Feature lists, as indicated by 65a–c in FIG. 4 and noted in step 48 of FIG. 2, are generated by the feature detection operations for the various features sought. These feature lists are then combined with other information about the workpiece to define a workpiece model 66 that is used by optimizer 30 to determine the cuts to be made.

Figure 10A:
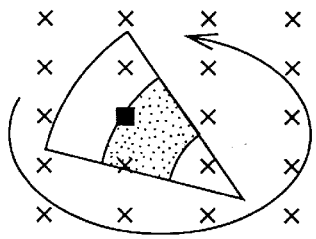
FIGS. 10A–B illustrate the method of FIG. 9.
Figure 10B:
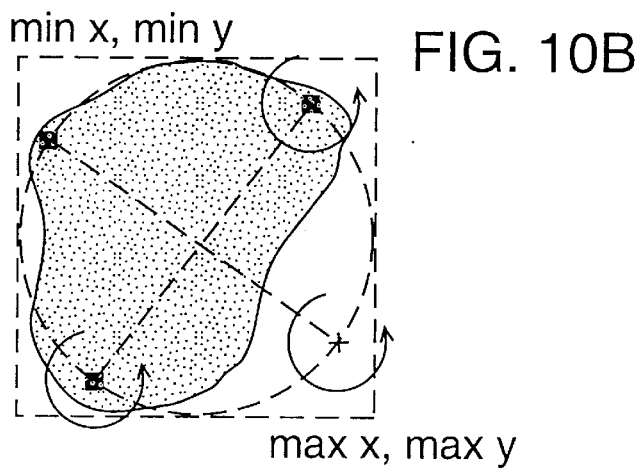

FIGS. 9 and 10 show the steps of one operation for detecting knots. The knot detection operation 90 utilizes a series of knot models of various sizes and orientations to determine if pixels in the image have the shape of a knot. In the preferred embodiment there are 12 orientations, 30 degrees apart, and five different-sized models. FIG. 10A shows an example of a knot model applied to a pixel of at least the threshold intensity. The model is pie-shaped, with a dark intermediate section and light outer section. The dark intermediate section corresponds to the enhanced pixels of the feature of interest. The model may be described geometrically. The knot models are applied to the pixel by "rotating" the different oriented models about the pixel and repeating this rotation for each of the different-sized models (step 91). As each model is applied a correlation K is determined, such as in the manner described in the "900 Series Programmer's Guide" by Acumen Incorporated (1991), which is hereby incorporated by reference. K measures the extent that the intensities of the neighboring pixels match the model. Each pixel of the grayscale image is correlated to each pixel of the model and the sum K is a metric of how well the image matches the model. The value K is then checked against a threshold T, and if it meets a threshold then there is a match between the model and the feature. The knot model with the highest correlation is selected for determining an ellipse (step 92). The center of the ellipse is determined by the tip of the knot. The ellipse's boundary is determined from the edge of the black portion of the model. And a rectangle with minimum and maximum x and y values is defined around the ellipse, as indicated in FIG. 10B.

With the ellipse defined, a check is made if all four "corner" pixels on the ellipse boundary have been checked (step 93). A corner pixel is one that is 90 degrees along an arc of the ellipse boundary. Each corner pixel is checked if it meets the threshold pixel intensity (step 94). If one does, then the knot models are also applied to that pixel in an attempt to identify the boundaries of the feature, whereby each model match may expand the boundaries of the min/max rectangle.

After all the corner pixel have been checked, a decision is made whether there is closure of the feature (step 95). Closure is determined when a sufficient degree of rotation of model matches if found with the min/max rectangle. In the present embodiment, closure requires that at all of the models contained in the list corresponding to a min/max rectangular area provide a contiguous rotation about a center of at least 270 degrees. Other tests could, of course, be used. If the pixels do, then the image area is considered a knot (step 97) and the minimum and maximum coordinates are preserved as an element of a feature list. FIG. 10B is an example of closure, with three of the corner pixels meeting the threshold intensity. If not, then the area is not considered a knot (step 96). The operation then proceeds in the same fashion through the rest of the image, adding detecting knots to the knot feature list.

Figure 12:
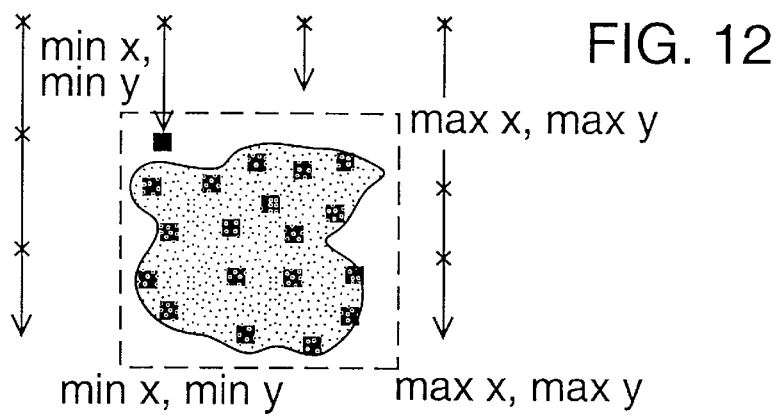
FIG. 12 illustrates the method of FIG. 9.
Figure 11:
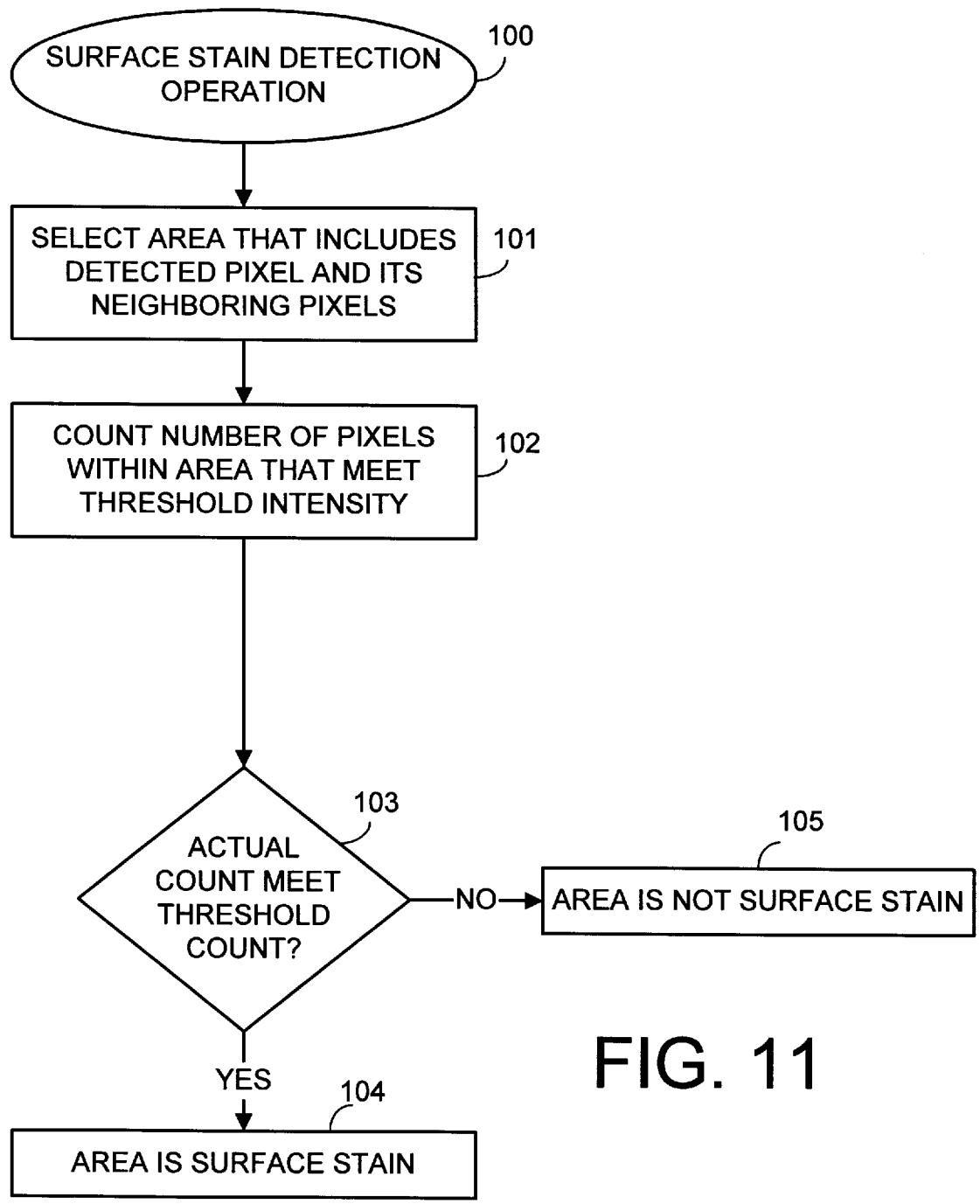
FIG. 11 is a flowchart for applying a surface stain operation to an image of a piece of wood.

FIGS. 11 and 12 show the steps of another feature detection operation 100 for detecting a board surface stain such as blue stain. Upon detection of a feature pixel, an area is selected that includes the detected pixel and its neighboring pixels (step 101). The area may be a square, for example, of 10 by 10 pixels. The operation proceeds to check each pixel in the square against the threshold intensity and count the total (step 102). This total is then compared against a threshold count for the area (step 103). For example, the threshold count for a square of 100 pixels might be 75. If the actual count meets the threshold count, then the area is considered surface stain (step 104) and the minimum and maximum coordinates are preserved for a surface stain feature list. If the actual count does not, then the area is not considered surface stain (step 105). The operation then proceeds through the rest of the image.

Figure 14:
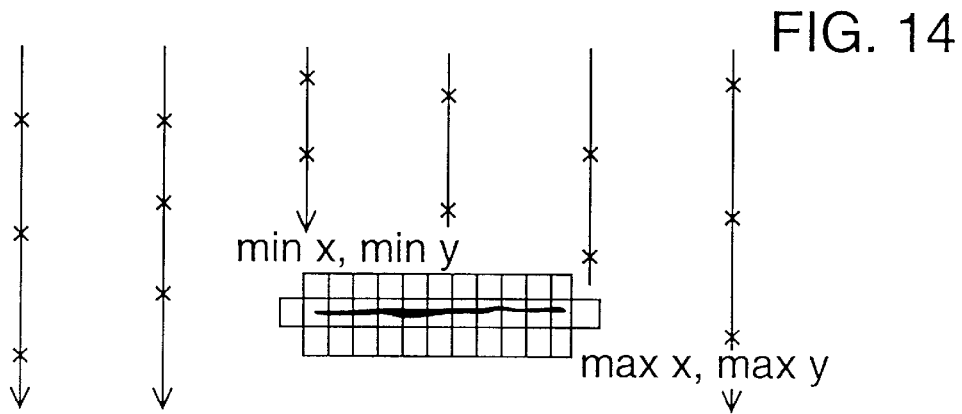
FIG. 14 illustrates the method of FIG. 13.
Figure 13:
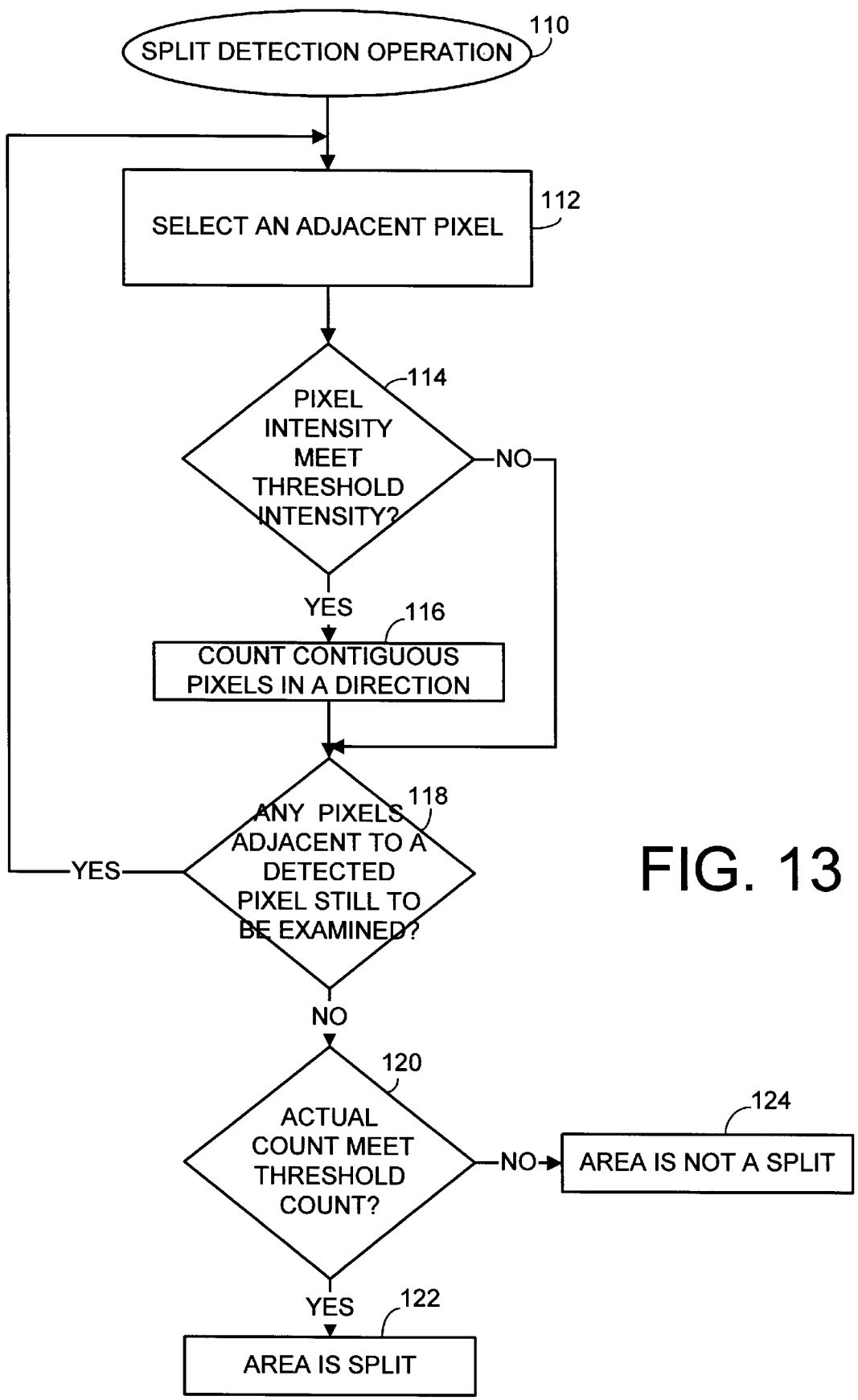
FIG. 13 is a flowchart for applying a split detection operation to an image of a piece of wood.

FIGS. 13 and 14 show the steps of another example operation 110 for detecting splits or cracks in boards. Upon detection of a pixel that meets the threshold intensity, the pixel is recorded and an adjacent pixel is selected for scrutiny (step 112). Two pixels are then examined using an edge operator, i.e., one pixel satisfies the threshold and one does not (step 114). If yes, the pixel is counted as detected (step 116). If no, the pixel is ignored. A check is then made if any pixels adjacent to a detected pixel is still to be examined (step 118). If so, the steps of selecting and examining are repeated until all of the surrounding pixels fail to meet the threshold intensity. The actual count is then checked to determine if it meets a threshold pixel count for a split (step 120). If yes, the area is considered a split (step 122). Minimum and maximum coordinates are established for the area and the area is added to a split feature list. If not, the area is not considered a split and is ignored (step 124).

Figure 3A:
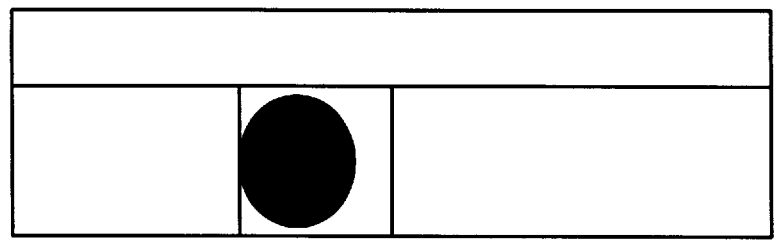
FIGS. 3A and B are examples of possible cut permutations for a workpiece with a defect, such as wood with a knot.
Figure 3B:
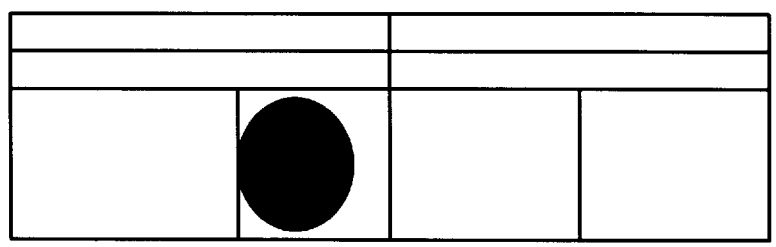

Returning to FIGS. 1 and 2, with the workpiece model at hand, optimizer 30 proceeds to determine what cuts to make to the workpiece. First it generates a list of cut permutations with market value from the workpiece model (step 50). FIGS. 3A and 3B are examples of such permutations. Note the knot in the lower center of the board and the different-sized products that may be cut from the piece. As input to this optimization stage, the optimizer is given the cut schedule (products that may be produced from the board) and the market values for the different products.

These permutations are passed to a weighted value selection stage (step 51) that combines weighted values with the market value for the products of the permutations to adjust the permutations' market value. For example, a weighted value for four-inch wide product might be less than one, lowering the products value, while the weighted value for a five-inch wide product might be greater than one, raising the product's market value. The weighted values are generated by the scheduler (step 54) described in more detail below.

Figure 15:
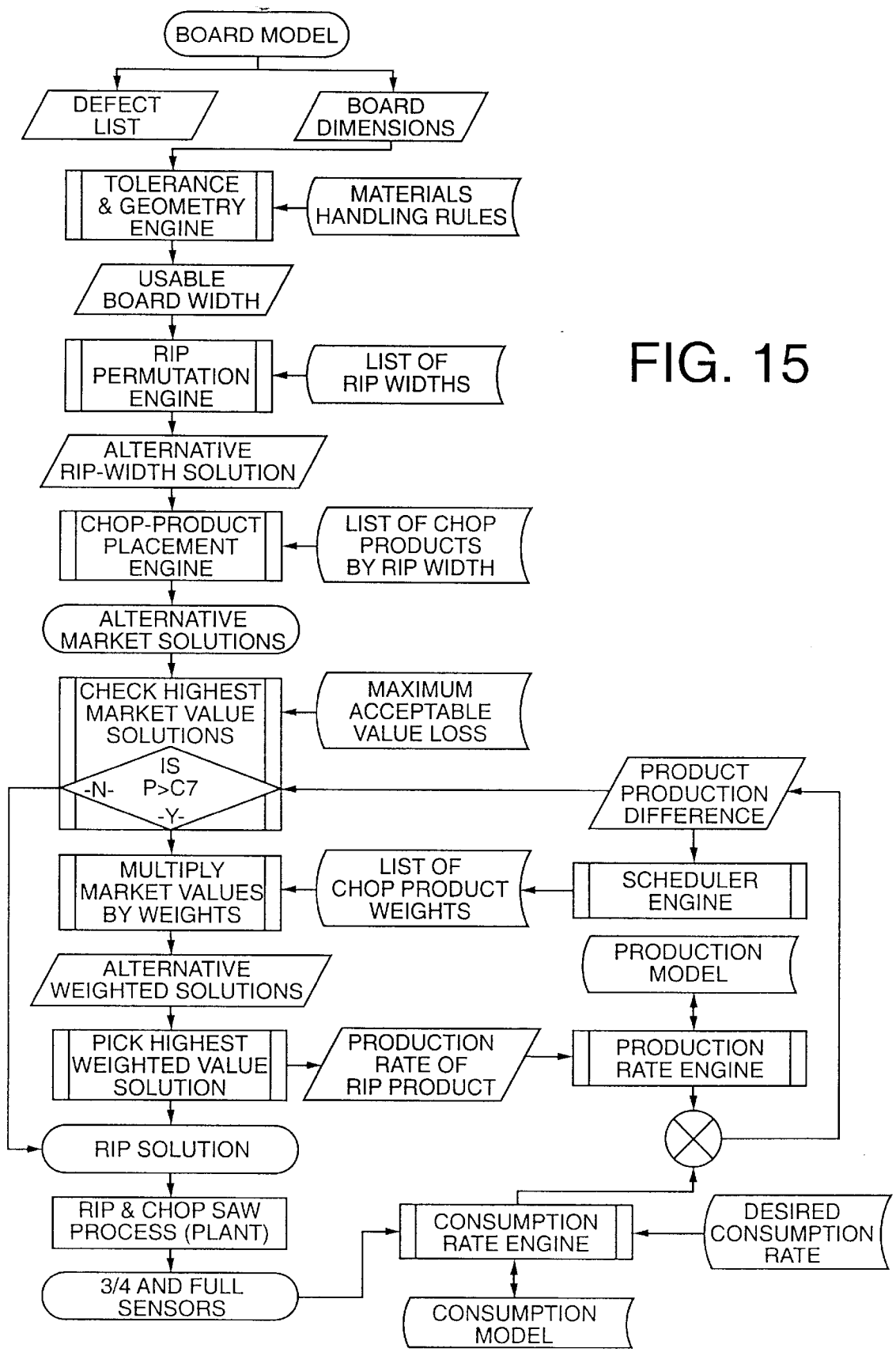
FIG. 15 is a flowchart of how the scheduler of FIG. 1 generates the weighted values for the optimizer, as indicated generally in FIG. 2.

If the market values solution's production is less than the rate of consumption, then the cut selector can make a local decision without using the weighted solution. In this fashion, the cut selector can make a decision that sacrifices consumption goals to make a desired product. This requires the cut selection engine to have a maximum value loss input for each product. That is, we choose a cut which violates the weighted solution because we can not sacrifice the value of a product(s) for production. Of course, this selection could also be determined after the weighted value calculation. The goal is not to make "blind" average weighted decisions that overlook a single valuable cut. See FIG. 15.

The optimizer also includes a cut selection stage (step 52) that generates the cut commands to the cutting device 34 such as a saw based on the adjusted market values of the permutations. In the present embodiment, the permutation with the highest adjusted market value is the one chosen for cuts.

As a last step, the workpiece is cut into products in accordance with the cut commands (step 53). These cuts are monitored by sensors at the cutting devices 34 and 36 and the information provided to scheduler 32 for generating weighted values. The information sensed included the present capacity of the cutting devices for cutting products of different sizes and the present rate at which products are being cut. describe scheduler algorithm with reference to drawing.

Having illustrated and described the principles of the invention in a preferred embodiment, it should be apparent to those skilled in the art that the preferred embodiment can be modified in arrangement and detail without departing from such principles. For example, many of the software aspects of the embodiment may be implemented in hardware and many of the hardware aspects may be implemented in software. In view of the many possible embodiments to which the principles of the invention may be applied, it should be recognized that the illustrated embodiment is only a preferred example of the invention and should not be taken as a limitation on the scope of the following claims. We claim as the invention all that comes within the scope of these claims.

We claim:

1. Apparatus for generating an image of a workpiece, comprising:

a reflective imaging system for generating a first bit image of a surface of the workpiece, the first image having a number of bits per pixel;

a transmissive imaging system for generating a second bit image of a density of the workpiece, the second image having a number of bits per pixel;

memory for storing the first and second bit images as a combined bit image of the workpiece, the combined bit image having a number of bits per pixel representing pixel intensity;

a filter for enhancing the combined bit image, the filter performing the following steps:

for a feature of interest, determining a mean, a standard deviation, and a normal distribution of the pixel intensities; and using the normal distribution to map the pixel intensities above the mean to one set of enhanced pixel intensities and to map pixel intensities below the mean to another set of enhanced pixel intensities; and memory for storing an image of the workpiece with the enhanced pixel intensities.

2. The apparatus of claim 1 wherein transmissive imaging system comprises an X-ray scanner for viewing the surface and interior density of the workpiece.

3. The apparatus of claim 1 wherein the transmissive imaging system comprises a microwave scanner for viewing the surface and interior density of the workpiece.

4. The apparatus of claim 1 wherein the filter performs its steps separately for each group of bits representing a color or density of the workpiece, and the mapped pixel intensities that result are combined to form the enhanced image.

5. The apparatus of claim 1 wherein the filter performs the additional steps of:

generating a histogram of the pixel intensities;

subtracting outer modes of higher and lower pixel intensities from the histogram;

wherein the mean, standard deviation, and normal distribution are determined from the remaining histogram.

6. The apparatus of claim 5 wherein the feature of interest is one with a lower pixel intensity and the filter performs the following steps:

subtracting the normal distribution from the original histogram to obtain lower pixel intensities outside the normal distribution;

adding back the previously subtracted mode of lower pixel intensity to the lower pixel intensities; and determining a mean, a standard deviation, and a normal distribution of the lower pixel intensities;

wherein the normal distribution of the lower pixel intensities is used to map pixel intensities above the mean to higher pixel intensities and to map pixel intensities below the mean to lower pixel intensities.

7. A method for generating an image of a surface stain in a wood workpiece, the method comprising the following steps;

generating a bit image of a surface of the workpiece, the image having a number of bits per pixel;

sampling pixels of the bit image to determine if a pixel meets a threshold intensity for the feature being sought;

for a pixel that meets the threshold intensity;

selecting an area of the bit image that includes the pixel and its neighboring pixels;

counting the number of pixels within the area that meet the threshold intensity; and determining if the area represents surface stain by comparing the count against a threshold count for the area.

8. A method for generating an image of a workpiece, the method comprising the following steps:

generating a first bit image of a surface of the workpiece, the first image having a number of bits per pixel;

generating a second bit image of a density of the workpiece, the second image having a number of bits per pixel;

combining the first and second bit images into a combined bit image of the workpiece, the image having a number of bits per pixel representing pixel intensity;

for a feature of interest in the combined bit image, determining a mean, a standard deviation, and a normal distribution of the pixel intensities;

using the normal distribution to map the pixel intensities above the mean to one set of enhanced pixel intensities and to map pixel intensities below the mean to another set of enhanced pixel intensities; and storing an image of the workpiece with the enhanced pixel intensities.

9. A computer-readable medium having computer-executable instructions for performing the steps of claim 8.

10. The method of claim 8 including the following steps:

obtaining the complete bit image of the workpiece, the image having a number of bits per pixel representing pixel intensity;

sampling pixels of the image to determine if a pixel meets a threshold intensity for the feature being sought;

for a pixel that meets the threshold intensity, applying a feature-detection operation to the pixel and its neighboring pixels to determine if the feature is present in the image and, if so, the extent of the feature.

11. The method of claim 8 including:

generating a histogram of the pixel intensities;

subtracting outer modes of higher and lower pixel intensities from the histogram;

wherein the mean, standard deviation, and normal distribution are determined from the remaining histogram.

12. The method of claim 11 wherein the feature of interest is one with a lower pixel intensity and the method includes:

subtracting the normal distribution from the original histogram to obtain lower pixel intensities outside the normal distribution;

adding back the previously subtracted mode of lower pixel intensity to the lower pixel intensities; and determining a mean, a standard deviation, and a normal distribution of the lower pixel intensities;

wherein the normal distribution of the lower pixel intensities is used to map pixel intensities above the mean to higher pixel intensities and to map pixel intensities below the mean to lower pixel intensities.

13. The method of claim 8 wherein the steps are performed separately for each group of bits representing a color or density of the workpiece, and the mapped pixel intensities that result are combined to form the enhanced image.

14. The method of claim 8 wherein a first group of the bits per pixel represent workpiece surface color and are derived from a reflective imaging system and a second group of the bits per pixel represent workpiece density and are derived from a transmissive imaging system.

15. Apparatus for generating an image of a workpiece, comprising:

a reflective imaging system generating a first color bit image of a surface of the workpiece, the first image having at least three different colors and a number of bits per color per pixel;

a transmissive imaging system generating a second bit image of a density of the workpiece, the second image having a number of bits per pixel; and memory combining the first and second bit images into a combined image of the workpiece.

16. The apparatus of claim 15 wherein the reflective imaging system generates a first color bit image with red, green, and blue components and the transmissive imaging system generates a second bit image with density scale components, the combined image having a number of bits per pixel representing pixel intensity in red, green, blue, and density scale.

17. A method for generating an image of a workpiece, the method comprising the following steps:

generating a first bit image of a surface of the workpiece, the first image having a number of bits per pixel;

generating a second bit image of a density of the workpiece, the second image having a number of bits per pixel;

combining the first and second bit images into a combined bit image of the workpiece, the image having a number of bits per pixel representing pixel intensity;

sampling pixels of the combined bit image to determine if a pixel meets a threshold intensity for the feature being sought;

for a pixel that meets the threshold intensity, rotating and scaling a feature-shaped image about the pixel and its neighboring pixels while comparing the feature-shaped image thereto; and determining from the comparisons whether the pixel and its neighboring pixels represent a feature and, if so, the pixel boundaries of the feature.

18. The method of claim 17 wherein the workpiece is wood and the feature being sought is a knot, and the step of applying a feature-detection operation comprises:

rotating and scaling a knot-shaped image about the pixel and its neighboring pixels while comparing the knot-shaped image thereto; and determining from the comparisons whether the pixel and its neighboring pixels represent a knot and, if so, the pixel boundaries of the knot.

19. The method of claim 17 including generating a list of the locations of the detected features in the image of the workpiece.

* * * * *

UNITED STATES PATENT AND TRADEMARK OFFICE
CERTIFICATE OF CORRECTION

PATENT NO. : 5,892,808
DATED : April 6, 1999
INVENTOR(S) : Goulding et al.

It is certified that error appears in the above-identified patent and that said Letters Patent is hereby corrected as shown below:

Col. 9, line 28, "intensity; should read --intensity: --.

Signed and Sealed this

Seventeenth Day of April, 2001

Attest:

NICHOLAS P. GODICI

Attesting Officer     Acting Director of the United States Patent and Trademark Office